United States Patent
Renninger

(10) Patent No.: US 10,357,095 B1
(45) Date of Patent: Jul. 23, 2019

(54) ENCAPSULATED DEHYDRATED SHAMPOO COMPRISING SODIUM LAURYL SULFOACETATE

(71) Applicant: Tiffany Ann Renninger, Mifflintown, PA (US)

(72) Inventor: Tiffany Ann Renninger, Mifflintown, PA (US)

( * ) Notice: Subject to any disclaimer, the term of this patent is extended or adjusted under 35 U.S.C. 154(b) by 134 days.

(21) Appl. No.: 15/694,898

(22) Filed: Sep. 4, 2017

(51) Int. Cl.
| | |
|---|---|
| *C11D 1/04* | (2006.01) |
| *A45D 37/00* | (2006.01) |
| *A61K 8/46* | (2006.01) |
| *A61K 8/9794* | (2017.01) |
| *A61K 8/365* | (2006.01) |
| *A61K 8/98* | (2006.01) |
| *A61K 8/19* | (2006.01) |
| *A61K 8/92* | (2006.01) |
| *A61K 8/81* | (2006.01) |
| *B29C 53/04* | (2006.01) |
| *B29C 53/00* | (2006.01) |
| *B65B 3/04* | (2006.01) |
| *B65B 7/08* | (2006.01) |
| *B65D 75/08* | (2006.01) |
| *B02C 19/08* | (2006.01) |
| *A61Q 5/02* | (2006.01) |
| *B29K 105/00* | (2006.01) |
| *B29K 29/00* | (2006.01) |
| *B29L 31/00* | (2006.01) |

(52) U.S. Cl.
CPC ............... *A45D 37/00* (2013.01); *A61K 8/19* (2013.01); *A61K 8/365* (2013.01); *A61K 8/463* (2013.01); *A61K 8/8129* (2013.01); *A61K 8/922* (2013.01); *A61K 8/9794* (2017.08); *A61K 8/986* (2013.01); *A61Q 5/02* (2013.01); *B02C 19/08* (2013.01); *B29C 53/005* (2013.01); *B29C 53/04* (2013.01); *B65B 3/04* (2013.01); *B65B 7/08* (2013.01); *B65D 75/08* (2013.01); *A61K 2800/87* (2013.01); *B29K 2029/04* (2013.01); *B29K 2105/256* (2013.01); *B29L 2031/7128* (2013.01)

(58) Field of Classification Search
CPC ....................................... C11D 1/04
See application file for complete search history.

(56) References Cited

U.S. PATENT DOCUMENTS

2006/0128592 A1* 6/2006 Ross .................... A61K 8/0208
510/439

* cited by examiner

*Primary Examiner* — Charles I Boyer
(74) *Attorney, Agent, or Firm* — John J. Elnitski, Jr.

(57) ABSTRACT

A crystalline shampoo, of a mixture comprising: one-quarter to three-quarter teaspoon of sodium lauryl sulfoacetate flake; one-eight to three-eights teaspoon of aloe vera leaf powder; one-eight to three-eights teaspoon of lactic acid; one-eight to three-eights teaspoon of olive oil; and 0.1 ml to 0.3 ml of essential oil. The mixture is encapsulated in a polyvinyl alcohol (PVA) sheet.

13 Claims, No Drawings

ENCAPSULATED DEHYDRATED SHAMPOO COMPRISING SODIUM LAURYL SULFOACETATE

BACKGROUND

The present invention generally relates to hair care products. More specifically, the present invention relates to shampoo.

There are many personal care products on the market for people, including hair care products such as shampoos. Shampoos use a high percentage of fresh water in production and are sold in containers that are usually plastic bottles. What would be better is if fresh water was reduced during manufacturing and the bottles were eliminated as well as the shampoo was sold in packaging that was environmentally friendly and dissolved during the use of the shampoo.

It is an object of the present invention to provide shampoo in an environmental friendly packaging that dissolves during use.

SUMMARY OF THE INVENTION

A crystalline shampoo, of a mixture comprising: one-quarter to three-quarter teaspoon of sodium lauryl sulfoacetate flake; one-eight to three-eights teaspoon of aloe vera leaf powder; one-eight to three-eights teaspoon of lactic acid; one-eight to three-eights teaspoon of olive oil; and 0.1 ml to 0.3 ml of essential oil. The mixture is encapsulated in a polyvinyl alcohol (PVA) sheet.

DETAILED DESCRIPTION

The present invention is an encapsulated dehydrated shampoo that is encapsulated in packaging that dissolves during use. The formula and method of making two different embodiments of a crystalline shampoo that is encapsulated in a dehydrated form will be presented.

The first embodiment is a moisturizing crystalline shampoo. The first embodiment ingredients include one-half teaspoon of sodium lauryl sulfoacetate flake; one-quarter teaspoon of aloe vera leaf powder; one-quarter teaspoon of lactic acid; one-quarter teaspoon of olive oil and four drops (0.2 ml) of essential oil. A example of the lactic acid is instant nonfat dry milk. Examples of essential oil are *Citrus aurantium dulcis*, tea tree (*Melaleusa alternifolio*), peppermint (*Mentha piperita*) or lavender (*Lavandula angustifolia*). The mixture of the first embodiment makes approximately one and one-half teaspoons of shampoo and the mixture can be increased proportionally as needed for the desired amount.

The second embodiment is a clarifying crystalline shampoo, which uses sodium bicarbonate as a substitute for the aloe vera leaf powder. The second embodiment ingredients include one-half teaspoon of sodium lauryl sulfoacetate flake; one-sixteenth teaspoon of sodium bicarbonate; one-quarter teaspoon of lactic acid; one-quarter teaspoon of olive oil and four drops (0.2 ml) of essential oil. A example of the sodium bicarbonate is baking soda. The mixture of the second embodiment makes approximately one teaspoon of shampoo and the mixture can be increased proportionally as needed for the desired amount.

The method of combining the ingredients for the first and second embodiments is as follows. First grind the dry milk in a mortar with a pestle. Place the dry ingredients of sodium lauryl sulfoacetate flake, and ground dry milk together in glass bowl. Add either the aloe vera leaf powder or sodium bicarbonate to the glass bowl. Then, add olive oil and essential oil to the glass bowl and stir the contents in the glass bowl to form the shampoo mixture. Finally, use the pestle to grind mixture together.

After the either the first or second embodiment is created, the mixture is then packaged by encapsulated in a polyvinyl alcohol (PVA) sheet. The polyvinyl alcohol (PVA) sheet will dissolve during the use of the encapsulated dehydrated shampoo. Encapsulation is as follows. Prepare a polyvinyl alcohol (PVA) sheet by wetting edges of two sides with dampened cotton swab. Fold the sheet slightly less than half and press together to create a pouch with one open end. Folding the sheet in this manner provides for one side of the pouch being longer than the other side of the pouch. Having one side of the pouch longer than the other side provides a top edge of the longer side that extends out further then the shorter side. Allow the pouch to dry. Pouches vary in size depending on amount of product needed. Typical sizes for the sheets are either 2½×1¾ inches or 2½×1½ inches. The size of the pouch and the amount of mixture to use varies with the type of hair. Thicker/coarser hair generally requires a pouch size of 2½×1¾ inches with one and one-half teaspoons of mixture. Normal/medium hair generally requires a pouch size of 2½×1½ inches with one teaspoon of mixture. Fine/thin hair generally requires a pouch size of 2½×1½ inches with one-half teaspoon of mixture. Place the mixture into the open end of the pouch. Wet top edge of the longer side of the pouch, fold over that top edge to close pouch and allow to dry. The mixture of shampoo is now encapsulated and ready to use by adding water and emulsifying with hands to dissolve the pouch and produce lather.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention that is to be given the full breadth of any and all equivalents thereof.

I claim:

1. A crystalline shampoo, comprising the following mixture of components:
    a) from one-quarter to three-quarters of a teaspoon of sodium lauryl sulfoacetate flake;
    b) from one-eighth to three-eighths of a teaspoon of a powder selected from the group consisting of an aloe vera leaf powder, sodium bicarbonate, or mixtures thereof;
    c) from one-eighth to three-eighths of a teaspoon of lactic acid;
    d) from one-eighth to three-eighths of a teaspoon of olive oil; and
    e) from 0.1 ml to 0.3 ml of essential oil.

2. The shampoo of claim 1, wherein there is one-half teaspoon of sodium lauryl sulfoacetate flake; one-quarter teaspoon of aloe vera leaf powder; one-quarter teaspoon of lactic acid; one-quarter teaspoon of olive oil and four drops of essential oil.

3. The shampoo of claim 1, wherein said lactic acid is supplied from instant nonfat dry milk.

4. The shampoo of claim 1, wherein said essential oils are one of *Citrus aurantium dulcis*, tea tree (*Melaleusa alternifolio*), peppermint (*Mentha piperita*) or lavender (*Lavandula angustifolia*).

5. The shampoo of claim 1, wherein said shampoo makes approximately one and one-half teaspoons of shampoo and can be increased proportionally as needed for the desired amount.

6. The shampoo of claim 1 wherein the shampoo is encapsulated in a polyvinyl alcohol (PVA) sheet to form a pouch.

7. The shampoo of claim 6, wherein said polyvinyl alcohol sheet is folded slightly less than half to provide a first side being longer than a second side to form a top edge of the longer side that extends out further and wherein said first side and said second side are press together to create a pouch with one open end and a flap.

8. The shampoo of claim 2 wherein the shampoo is encapsulated in a polyvinyl alcohol (PVA) sheet to form a pouch.

9. The shampoo of claim 8, wherein said polyvinyl alcohol sheet is folded slightly less than half to provide a first side being longer than a second side to form a top edge of the longer side that extends out further and wherein said first side and said second side are press together to create a pouch with one open end and a flap.

10. A method of making a crystalline shampoo comprising:
    a) grinding a lactic acid;
    b) mixing in sodium lauryl sulfoacetate flake with the ground lactic acid;
    c) mixing in aloe vera leaf powder and/or sodium bicarbonate to the sodium lauryl sulfoacetate flake and the lactic acid mixture;
    d) adding and stirring in olive oil and essential oil into the sodium bicarbonate and/or aloe vera leaf powder, sodium lauryl sulfoacetate flake and the lactic acid mixture to form the shampoo; and
    e) grind the final mixture.

11. The method of claim 10, wherein there is from one-quarter to three-quarters of a teaspoon of sodium lauryl sulfoacetate flake; from one-eighth to three-eighths of a teaspoon of aloe vera leaf powder; from one-eighth to three-eighths of a teaspoon of lactic acid; from one-eighth to three-eighths of a teaspoon of olive oil; and from 0.1 ml to 0.3 ml of essential oil.

12. The method of claim 10, further including the step of encapsulating the final shampoo mixture in a polyvinyl alcohol (PVA) sheet to form a pouch.

13. The method of claim 12, wherein said polyvinyl alcohol (PVA) sheet is prepared by wetting edges of two sides with a dampened material; folding the sheet slightly less than half and pressing together to create a pouch with one open end to provide one side of the pouch being longer than the other side of the pouch; allowing the pouch to dry; placing the final mixture into the open end of the pouch; wetting the top edge of the longer side of the pouch and folding over that top edge to close pouch; and allow the pouch to dry.

* * * * *